United States Patent [19]
Cilento et al.

[11] 4,204,540
[45] May 27, 1980

[54] OSTOMY COMPOSITION

[75] Inventors: Rudolfo D. Cilento, North Brunswick; Anthony L. La Via; James L. Chen, both of East Brunswick; John A. Hill, New Brunswick, all of N.J.

[73] Assignee: E. R. Squibb & Sons, Inc., Princeton, N.J.

[21] Appl. No.: 33,352

[22] Filed: Apr. 26, 1979

Related U.S. Application Data

[62] Division of Ser. No. 804,692, Jun. 8, 1977, Pat. No. 4,166,051.

[51] Int. Cl.$^2$ ............................................... A61F 5/44
[52] U.S. Cl. ............................................... 128/283
[58] Field of Search ............................... 128/155–156, 128/283, 295

[56] References Cited

U.S. PATENT DOCUMENTS

| | | | |
|---|---|---|---|
| 3,339,546 | 9/1967 | Chen | 128/283 |
| 3,877,431 | 4/1975 | Kross | 128/283 |
| 3,906,951 | 9/1975 | Chen | 128/283 |
| 3,908,658 | 10/1975 | Marsan | 128/283 |
| 3,972,328 | 8/1976 | Chen | 128/283 |
| 3,980,084 | 9/1976 | Kross | 128/283 |
| 4,007,263 | 2/1977 | Pichierri | 128/283 |
| 4,166,051 | 8/1979 | Cilento et al. | 128/283 |

OTHER PUBLICATIONS

*Adhesion in Biological Systems*, Chap. 10, Chen et al., Academic Press 1970.

*Primary Examiner*—Robert W. Michell
*Assistant Examiner*—C. F. Rosenbaum
*Attorney, Agent, or Firm*—Lawrence S. Levinson; Stephen B. Davis

[57] ABSTRACT

A composition adapted for use around the stoma consisting of a homogeneous mixture of a pressure sensitive adhesive component, mineral oil, and hydrocolloid gums or cohesive strengthening agents or a mixture of hydrocolloid gums and cohesive strengthening agents. By controlling the amount of mineral oil the resulting composition can be easily shaped according to the particular need.

20 Claims, No Drawings

OSTOMY COMPOSITION

This is a division of application Ser. No. 804,692, filed June 8, 1977 and now U.S. Pat. No. 4,166,051.

BACKGROUND OF THE INVENTION

Major abdominal surgery for a number of diseases involving different parts of the gastro-intestinal and urinary tract can result in the patient being left with an abdominal stoma. The three most common types of abdominal stoma are the colostomy, the ileostomy, and the ileal conduit. In the case of an ileostomy, ileal conduit, and many colostomy operations, the patient is unable to control the passage of bodily waste material and must rely upon an appliance attached to their body to collect this material.

These appliances can be attached directly to the body by means of an adhesive faceplate or mounting gasket or can be attached to an ostomy washer or skin barrier which is fitted around the stoma.

A mounting gasket including a sealing ring formed from a karaya-glycerol gel is described by Marsan in U.S. Pat. No. 3,302,647. Ostomy washers formed of other materials have been taught in the art. For example, Etes in U.S. Pat. No. 3,640,741 discloses a washer formed of a cross-linked alginate or carboxymethylcellulose gum, Pratt in U.S. Pat. No. 3,612,053 describes an ostomy sealing washer formed from an oil-extended block copolymer having a water activatable adhesive on one surface, Marsan in U.S. Pat. Nos. 3,712,304 and 3,799,166 describes an ostomy seal made from starch and gelatinized starch cross-linked with glyoxal, Marsan in U.S. Pat. No. 3,878,847 describes a thin membrane that contacts the stoma, Marsan in U.S. Pat. No. 3,908,658 describes an ostomy seal formed from a gel of mineral oil, stryene-isobutylene copolymer and an ethylene-vinyl acetate copolymer, and Kross in U.S. Pat. Nos. 3,877,431 and 3,980,084 describes ostomy seals formed from polymeric materials.

Chen in U.S. Pat. No. 3,339,546 describes a bandage having an adhesive layer consisting of a mixture of gelatin, pectin, sodium carboxymethylcellulose, and polyisobutylene and a water insoluble polyethylene film which is currently employed as a skin barrier by ostomates. Other commercially available skin barriers contain a cloth mesh layer or polyethylene web sandwiches between two adhesive layers. The adhesive layers comprise a conventional pressure sensitive adhesive and a hydrocolloid.

In employing any of these systems it is difficult for the ostomate to achieve a tight fluid proof seal between the mounting gasket, washer, and/or skin barrier and the stoma. Leakage of the corrosive effluent from the stoma will eventually cause disintegration of the mounting gasket, washer, or skin barrier necessitating removal of the appliance. Also, this erosion can permit the corrosive effluent to contact the skin contiguous to the stoma causing serious irritation.

Ostomates having this problem employ various products to fill the area between the stoma and the gasket, washer, and/or skin barrier. Karaya powder is the most widely used product at this time. Various ointment or paste type products have been suggested and used by ostomates to protect the area of skin contiguous to the stoma including those taught by Steinhardt in U.S. Pat. No. 3,029,187, Cyr et al. in U.S. Pat. No. 3,029,188, Chen in U.S. Pat. No. 3,906,951, and Pichierri in U.S. Pat. No. 4,007,263.

Another problem facing many ostomates involves the actual attachment of the appliance. In order to secure the appliance and achieve a tight fit around the stoma, it is desirable that the body surface be relatively flat and smooth. An ostomate whose abdomen is flabby or who has scar tissue as a result of surgery may need to contruct a platform type of dressing by piecing together a skin barrier. The construction of such a dressing is both time consuming and expensive.

SUMMARY OF THE INVENTION

This invention is directed to a composition adapted for use by an ostomate. The composition is a homogeneous mixture of a pressure sensitive adhesive component, mineral oil, and hydrocolloid gums or cohesive strengthening agents or a mixture of hydrocolloid gums and cohesive strengthening agents.

The composition can be shaped so as to fill the area between the stoma and a mounting gasket, ostomy washer, and/or skin barrier. Also, the composition can be employed to build-up an area of the abdomen around the stoma so as to provide a relatively flat and smooth surface to which an appliance or skin barrier can be securely attached.

DETAILED DESCRIPTION

The components of the composition of this invention are selected to obtain the desired balance of plasticity, cohesive strength, and tack. The composition differs from the relatively rigid ostomy washers and the amorphous ointments, pastes, or powders described above in that it has a putty-like consistency which permits it to be easily shaped by hand and fitted around the stoma or used to build-up an area of the abdomen under a skin barrier. Since the composition is contacting the body around the stoma it must not contain ingredients which will irritate this already sensitive area of skin.

The composition should be tacky so as to aid in securing the appliance or skin barrier to the body but must not be so sticky that it can not be easily shaped by hand. The composition must possess sufficient elasticity so that when in place on the abdomen it can follow changes in contour and shape caused by movement of the ostomate. The composition should resist disintegration caused by contact with effluent leaked from the stoma.

The composition of this invention can be viewed as being a homogeneous mixture of a plasticizing agent and a homogeneous premix including a pressure sensitive adhesive component and hydrocolloid gums or cohesive strengthening agents or a mixture hydrocolloid gums and cohesive strengthening agents.

The pressure sensitive adhesive component of the composition provides dry adhesion or dry tack and holds the entire composition together. Various natural or synthetic viscous substances either possessing dry tack by themselves or developing such tack upon the addition of a plasticizer such as natural rubber, silicone rubber, acrylonitrile rubber, polyurethane rubber, polyisobutylenes, etc., are suitable for this purpose. Low molecular weight polyisobutylenes having a viscosity average molecular weight of from about 36,000 to about 58,000 (Flory) are preferred. Such polyisobutylenes are commercially available under the trademark Vistanex from Exxon Co. as grades LM-MS and LM-MH. Optionally, in order to increase the elasticity and flexibility of the composition elastomeric polymers such as medium molecular weight polyisobutylenes having a viscosity average molecular weight of from about 1,150,000 to 1,600,000 (Flory) or butyl rubber which is a copolymer of isobutylene with a minor amount of isoprene having a viscosity average molecular weight of from about 300,000 to about 450,000 (Flory) can be added. Butyl rubber having a viscosity average molecular weight of about 425,000 (commercially available as grade 077) is preferred. The elastomer can be added in amounts of up to about 30% by weight of the pressure sensitive adhesive. The pressure sensitive adhesive and the optionally added elastomer together should be from about 40% to about 60% by weight of the premix.

Preferably, the low molecular weight polyisobutylene pressure sensitive adhesive and the higher molecular weight butyl rubber elastomer are employed in a ratio of from about 3 to 1 to about 5 to 1 on a weight basis, 4 to 1 being most preferred, and the combination is present at from about 45% to about 55% by weight of the premix.

Chen in U.S. Pat. No. 3,339,546 disclosed the incorporation of various water soluble or swellable hydrocolloids in an adhesive composition. It was felt that these hydrocolloid materials would absorb moisture such as perspiration and provide wet adhesion or wet tack for the composition. It has been found that certain hydrocolloid gums while possessing the ability to absorb such moisture, in fact, are not suitable for use within the composition since upon swelling they turn into a soft gelatinous mass. This swelling and loss of consistency can cause the composition to erode and disintegrate.

Thus, if a hydrocolloid gum is included within the premix it should have a large capacity to absorb moisture, should provide wet adhesion, and should also hydrate and swell at a relatively slow rate so as not to cause disintegration of the composition. Guar gum, locust bean gum, and mixtures thereof have been found to be suitable with guar being preferred and such gums can be present at up to about 40% by weight of the premix.

An additional gum substance having soothing or healing properties can be included within the premix. Pectin, gum karaya, and mixtures thereof have been found to be suitable with pectin being preferred and can be present at from 0% to about 25% by weight of the premix provided that the total amount of gums within the premix is no more than about 60% by weight, preferably up to 55%.

A cohesive strengthening agent can be included within the premix. Such agents while not providing any wet tack function similarly to the hydrocolloid in absorbing moisture and thus decreasing the tendency of the composition to erode and disintegrate. Also, when combined with hydrocolloid gums the cohesive strengthening agent will control the swelling of the gum and lessen the rate of disintegration. Of course, the cohesive strengthening agent employed in the premix must also result in a final composition having the desired consistency after addition of the plasticizing agent. Suitable cohesive strengthening agents are finely divided cellulose materials including purified wood cellulose such as that available commercially under the trademark Solka-Floc and microcrystalline cellulose such as that available commercially under the name Avicel, finely divided substantially water insoluble cross-linked dextran such as that available commercially under the trademark Sephadex, finely divided substantially water insoluble cross-linked sodium carboxymethylcellulose such as that available commercially under the trademark Aqualon or that described in U.S. Pat. No. 3,589,364 and available commercially from The Buckeye Cellulose Corp., and a finely divided substantially water insoluble starch-acrylonitrile graft copolymer such as that described in U.S. Pat. No. 3,661,815 and commercially available from the Grain Processing Corp. These materials can be present at up to about 60% by weight of the premix, preferably 55%. Purified wood cellulose is the preferred cohesive strengthener.

If desired, the premix can include a mixture of one or more hydrocolloid gums and one or more cohesive strengthening agents. Such a mixture should be present at from about 40% to about 60% by weight of the premix, preferably 45% to 55%.

Small amounts, i.e. less than 5% by weight of the premix, of other ingredients can be also included. For example, an antioxidant such as butylated hydroxyanisole, a deodorant, or a perfume agent can be included.

The premix is prepared by forming a homogeneous dispersion of the pressure sensitive adhesive component and the elastomer with a heavy duty mixer, e.g. a kneader mixer or sigma blade mixer. The hydrocolloid gums, cohesive strengthening agent, and any other optional ingredients are added and mixing is continued until a homogeneous dough is formed. Alternatively, the elastomer is first broken down by mixing for several minutes, a portion of the pressure sensitive adhesive and other ingredients are added and mixing continued until a homogeneous mass is formed. The balance of the pressure sensitive adhesive is then added and the mixing continued until a homogeneous dough is formed. This dough is a relatively tough cohesive mass.

In order to prepare a composition which can be easily shaped by hand a plasticizing agent is added to the premix. The plasticizing agent must be compatible with the ingredients in the premix and, in particular, must not impair the dry tack resulting from the pressure sensitive adhesive component of the premix. Mineral oil is the preferred plasticizer. The mineral oil and the premix are present in the final composition in a ratio of from about 1 to 10 to about 3.5 to 10 on a solids weight basis. If an insufficient amount of mineral oil is added the composition will be too tough to shape by hand and if too much mineral oil is added the composition becomes sticky and difficult to handle.

The final composition is prepared by gradually adding the mineral oil to the doughy premix while continuously mixing until a homogeneous product is obtained. This composition can be packaged as bulk in jars or shaped and packaged in smaller amounts.

The following examples are illustrative of the invention. Other suitable adhesive composition can be obtained by minor variations in the amounts of ingredients employed.

EXAMPLE 1

This example is directed to preparing a composition consisting of mineral oil and a premix.

| Premix Ingredients | Percent by weight of the premix |
|---|---|
| Polyisobutylene of a viscosity | |

-continued

| Premix Ingredients | Percent by weight of the premix |
|---|---|
| average molecular weight (Flory) of 36,000 to 45,000 (Vistanex LM-MS of Exxon) | |
| Butyl rubber of a viscosity average molecular weight (Flory) of 425,000 (Exxon grade 077) | 10 |
| Guar gum of high grade extra fine powder (Jaquar A-40-F of Stein Hall Co.) | 30 |
| Finely divided purified wood cellulose (Solka-Floc BW-100 of Brown Co.) | 20 |
| | 100 |

1.6 kg. of butyl rubber is broken down by mixing in a kneader mixer for two to five minutes. 3.2 kg. of the low molecular weight polyisobutylene is added and mixed with the butyl rubber for two to five minutes. 4.8 kg. of guar gum and 3.2 kg. of the finely divided purified wood cellulose are combined in a powder mixer and the resulting powder is added to the polyisobutylene-butyl rubber mixture. Mixing of the ingredients is continued until a homogeneous mass is formed with the polyisobutylene and butyl rubber completely interdispersed (about 10 to 20 minutes). The remaining 3.2 kg. of the low molecular weight polyisobutylene is added and mixing is continued until a homogeneous dough is formed (about 10 to 20 minutes).

The resulting 16 kg. of premix is combined with 4 kg. of mineral oil. The mineral oil is added gradually over the course of about 15 to 20 minutes with continuous stirring until a homogeneous mass is formed.

EXAMPLES 2 TO 33

Following the procedure of example 1 but employing the following ingredients other compositions within the scope of the invention are obtained.

| | PREMIX | | | | | | | |
|---|---|---|---|---|---|---|---|---|
| Ex. | Polyisobutylenes (4:1 ratio of Vistanex LM-MS and butyl rubber grade 077) | Guar gum | Locust bean gum | Pectin | Karaya | Purified wood cellulose (Solka-Floc) | Micro-crystalline cellulose (Avicel) | Mineral oil (Ratio of mineral oil to premix in final composition) |
| 2 | 50% | 20% | — | — | — | 30% | — | 3 to 10 |
| 3 | 50% | 30% | — | 20% | — | — | — | 1 to 4 |
| 4 | 50% | — | — | — | — | 50% | — | 3.5 to 10 |
| 5 | 45% | 35% | — | — | 20% | — | — | 1 to 5 |
| 6 | 50% | 20% | — | 10% | — | 20% | — | 1 to 10 |
| 7 | 40% | 30% | — | 20% | — | 10% | — | 3 to 10 |
| 8 | 50% | 15% | — | 15% | — | 20% | — | 1 to 4 |
| 9 | 50% | 25% | — | 10% | — | 15% | — | 1 to 5 |
| 10 | 40% | 20% | — | — | — | 40% | — | 3 to 10 |
| 11 | 50% | 35% | — | — | — | — | 15% | 1.5 to 10 |
| 12 | 45% | 35% | — | 20% | — | — | — | 1 to 4 |
| 13 | 45% | 35% | — | — | — | — | 20% | 1 to 5 |
| 14 | 50% | — | 30% | — | — | 20% | — | 1 to 4 |
| 15 | 50% | — | 20% | — | — | 30% | — | 1 to 3 |
| 16 | 50% | 20% | 10% | — | — | 20% | — | 3 to 10 |
| 17 | 40% | 20% | — | 15% | 15% | 10% | — | 3.5 to 10 |
| 18 | 60% | — | — | — | — | — | 40% | 1 to 4 |
| 19 | 45% | — | 35% | — | — | 20% | — | 1 to 5 |
| 20 | 50% | — | 20% | 10% | — | 20% | — | 3.5 to 10 |

| | PREMIX | | | | | | |
|---|---|---|---|---|---|---|---|
| Ex. | Polyisobutylenes (4:1 ratio of Vistanex LM-MS and butyl rubber grade 077) | Guar gum | Locust bean gum | Pectin | Karaya | Cross-linked sodium carboxymethyl-cellulose (Hercules Aqualon R or Buckeye Cellulose Corp. CLD) | Mineral oil (ratio of mineral oil to premix in final composition) |
| 21 | 50% | 35% | — | — | — | 15% | 3 to 10 |
| 22 | 45% | 35% | — | — | — | 20% | 1 to 4 |
| 23 | 40% | — | 25% | 25% | — | 10% | 1 to 5 |
| 24 | 55% | — | — | — | — | 45% | 3 to 10 |
| 25 | 45% | 25% | — | — | 20% | 10% | 1 to 4 |

| | PREMIX | | | | | | | |
|---|---|---|---|---|---|---|---|---|
| Ex. | Polyisobutylenes (4:1 ratio of Vistanex LM-MS and butyl rubber grade 077) | Guar gum | Locust bean gum | Pectin | Karaya | Cross-linked dextran (Sephadex CM-C50) | Starch-acrylonitrile graft copolymer (Grain Processing Corp. Polymer 35-A-100) | Mineral oil (ratio of mineral oil to premix in final composition) |
| 26 | 50% | 20% | — | — | — | — | 30% | 3 to 10 |
| 27 | 50% | 40$ | — | — | 10% | — | — | 1 to 4 |
| 28 | 50% | 35% | — | — | — | — | 15% | 3.5 to 10 |
| 29 | 50% | — | 10% | — | — | — | 40% | 3 to 10 |
| 30 | 50% | 20% | — | 10% | — | 20% | — | 1 to 4 |
| 31 | 40% | 30% | — | 20% | — | 10% | — | 1 to 10 |
| 32 | 50% | 15% | — | — | — | 35% | — | 1 to 5 |
| 33 | 60% | — | — | — | — | 40% | — | 3 to 10 |

What is claimed is:

1. The method of protecting the area of skin between the stoma and an attached appliance, faceplate, or skin barrier which comprises shaping and placing around the stoma the shaped mass which comprises a homogeneous mixture of mineral oil and a premix in a ratio of from about 1 to 10 to about 3.5 to 10 on a solids weight basis; wherein said premix comprises a homogeneous mixture of (A) from about 40% to about 60% by weight of a mixture of a pressure sensitive adhesive and an optional elastomer wherein said adhesive is a low molecular weight polyisobutylene and said elastomer if present is a medium molecular weight polyisobutylene or butyl rubber at up to about 30% by weight of said low molecular weight polyisobutylene and (B) from about 40% to about 60% by weight of a second component which is a mixture of one or more hydrocolloid gums, a cohesive strengthening agent, or a mixture of hydrocolloid gums and cohesive strengthening agent wherein said hydrocolloid gums are up to about 40% by weight of guar gum, locust bean gum, or mixtures thereof and from 0% to about 25% by weight of pectin, gum karaya, or mixtures thereof; and wherein said cohesive strengthening agent is finely divided cellulose, finely divided substantially water insoluble crosslinked dextran, finely divided substantially water insoluble sodium carboxymethycellulose, or finely divided substantially water insoluble starch-acrylonitrile graft copolymer.

2. The method of claim 1 wherein said pressure sensitive adhesive is a polyisobutylene having a viscosity average molecular weight of from about 36,000 to 58,000 on the Flory scale and said elastomer is a butyl rubber having a viscosity average molecular weight of about 425,000 on the Flory scale, said polyisobutylene and said butyl rubber being combined in a ratio of from about 3 to 1 to about 5 to 1 on a weight basis.

3. The method of claim 2 wherein said hydrocolloid gums if present are up to 40% by weight guar gum and from 0% to about 25% by weight pectin and said cohesive strngthening agent if present is purified wood cellulose.

4. The method of claim 3 wherein said premix comprises a homogeneous mixture of (A) from about 45% to about 55% by weight of a mixture of said low molecular weight polyisobutylene and said butyl rubber combined in a ratio of about 4 to 1 on a weight basis and (B) from about 45% to 55% by weight of a second component which is a mixture of hydrocolloid gums, purified wood cellulose, or a mixture of hydrocolloid gums and purified wood cellulose wherein said hydrocolloid gums are up to about 40% by weight of guar gum and from 0% to about 25% by weight of pectin.

5. The method of claim 4 wherein said premix comprises about 40% by weight of polyisobutylene having a viscosity average molecular weight of from about 36,000 to about 45,000 on the Flory scale, about 10% by weight of butyl rubber having a viscosity average molecular weight of about 425,000 on the Flory scale, about 30% by weight of guar gum, and about 20% by weight of finely divided purified wood cellulose.

6. The method of claim 5 wherein said mineral oil and said premix are combined in a ratio of about 1 to 4 on a solids weight basis.

7. The method of claim 4 wherein said premix comprises about 40% by weight of polyisobutylene having a viscosity average molecular weight of from about 36,000 to about 45,000 on the Flory scale, about 10% by weight of butyl rubber having a viscosity average molecular weight of about 425,000 on the Flory scale, about 30% by weight of guar gum, and about 20% by weight of pectin.

8. The method of claim 7 wherein said mineral oil and said premix are combined in a ratio of about 1 to 4 on a solids weight basis.

9. The method of calim 4 wherein said premix comprises about 40% by weight of polyisobutylene having a viscosity average molecular weight of from about 36,000 to about 45,000 on the Flory scale, about 10% by weight of butyl rubber having a viscostiy average molecular weight of about 425,000 on the Flory scale, and about 50% by weight of finely divided purified wood cellulose.

10. The method of claim 9 wherein said mineral oil and said premix are combined in a ratio of from about 3.5 to 10 on a solids weight basis.

11. The method of providing a smooth abdominal surface around the stoma for attachment of a skin barrier or appliance which comprises shaping and applying over any rough areas in the abdominal surface the shaped mass which comprises a homogeneous mixture of mineral oil and a premix in a ratio of from about 1 to 10 to about 3.5 to 10 on a solids weight basis, wherein said premix comprises a homogeneous mixture of (A) from about 40% to about 60% by weight of a mixture of a pressure sensitive adhesive and an optional elastomer wherein said adhesive is a low molecular weight polyisobutylene and said elastomer if present is a medium molecular weight polyisobutylene or butyl rubber at up to about 30% by weight of said low molecular weight polyisobutylene and (B) from about 40% to about 60% by weight of a second component which is a mixture of one or more hydrocolloid gums, a cohesive strengthening agent, or a mixture of hydrocolloid gums and cohesive strengthening agent wherein said hydrocolloid gums are up to about 40% by weight of guar gum, locust bean gum, or mixtures thereof and from 0% to about 25% by weight of pectin, gum karaya, or mixtures thereof; and wherein said cohesive strengthening agent is finely divided cellulose, finely divided substantially water insoluble crosslinked dextran, finely divided substantially water insoluble sodium carboxymethylcellulose, or finely divided substantially water insoluble starch-acrylonitrile graft copolymer.

12. The method of claim 11 wherein said pressure sensitive adhesive is a polyisobutylene having a viscosity average molecular weight of from about 36,000 to 58,000 on the Flory scale and said elastomer is a butyl rubber having a viscosity average molecular weight of about 425,000 on the Flory scale, said polyisobutylene and said butyl rubber being combined in a ratio of from about 3 to 1 to about 5 to 1 on a weight basis.

13. The method of claim 12 wherein said hydrocolloid gums if present are up to 40% by weight guar gum and from 0% to about 25% by weight pectin and said cohesive strengthening agent if present is purified wood cellulose.

14. The method of claim 13 wherein said premix comprises a homogeneous mixture of (A) from about 45% to about 55% by weight of a mixture of said low molecular weight polyisobutylene and said butyl rubber combined in a ratio of about 4 to 1 on a weight basis and (B) from about 45% to 55% by weight of a second component which is a mixture of hydrocolloid gums, purified wood cellulose, or a mixture of hydrocolloid gums and purified wood cellulose wherein said hydrocolloid gums are up to about 40% by weight of guar gum and from 0% to about 25% by weight of pectin.

15. The method of claim 14 wherein said premix comprises about 40% by weight of polyisobutylene having a viscosity average molecular weight of from about 36,000 to about 45,000 on the Flory scale, about 10% by weight of butyl rubber having a viscosity average molecular weight of about 425,000 on the Flory scale, about 30% by weight of guar gum, and about 20% by weight of finely divided purified wood cellulose.

16. The method of claim 15 wherein said mineral oil and said premix are combined in a ratio of about 1 to 4 on a solids weight basis.

17. The method of calim 14 wherein said premix comprises about 40% by weight of polyisobutylene having a viscosity average molecular weight of from about 36,000 to about 45,000 on the Flory scale, about 10% by weight of butyl rubber having a viscosity average molecular weight of about 425,000 on the Flory scale, about 30% by weight of guar gum, and about 20% by weight of pectin.

18. The method of calim 17 wherein said mineral oil and said premix are combined in a ratio of about 1 to 4 on a solids weight basis.

19. The method of calim 14 wherein said premix comprises about 40% by weight of polyisobutylene having a viscosity average molecular weight of from about 36,000 to about 45,000 on the Flory scale, about 10% by weight of butyl rubber having a viscosity average molecular weight of about 425,000 on the Flory scale, and about 50% by weight of finely divided purified wood cellulose.

20. The method of calim 19 wherein said mineral oil and said premix are combined in a ratio of from about 3.5 to 10 on a solids weight basis.

* * * * *

UNITED STATES PATENT AND TRADEMARK OFFICE
CERTIFICATE OF CORRECTION

PATENT NO. : 4,204,540

DATED : May 27, 1980

INVENTOR(S) : Rudolfo D. Cilento, Anthony L. LaVia, James L. Chen, John A. Hill

It is certified that error appears in the above—identified patent and that said Letters Patent is hereby corrected as shown below:

Col. 5, line 6, under Percent by weight of the premix should be inserted -- 40 --.

Signed and Sealed this

Twenty-first Day of October 1980

[SEAL]

Attest:

SIDNEY A. DIAMOND

Attesting Officer

Commissioner of Patents and Trademarks